Figure 1:
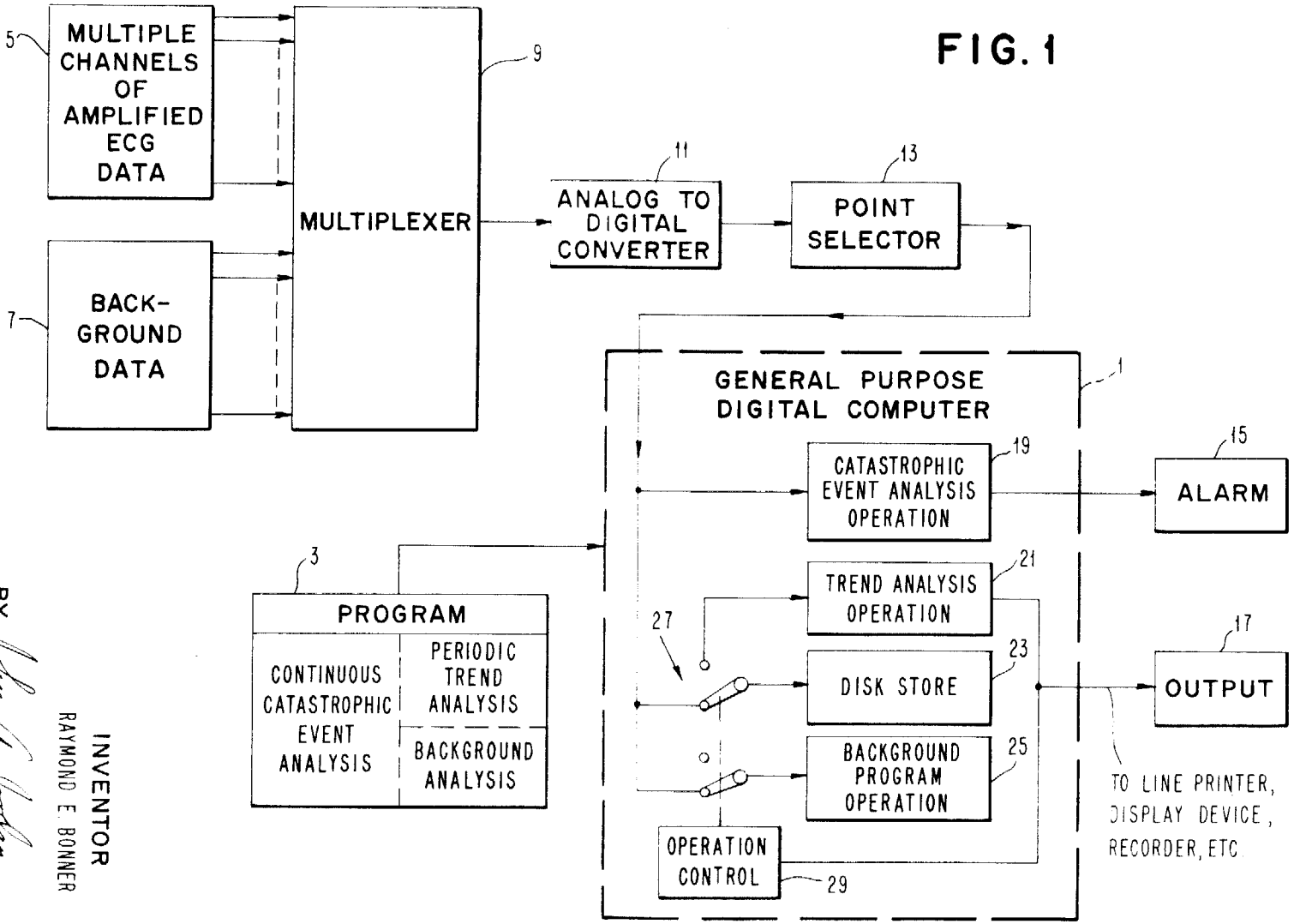
Figure 2A:
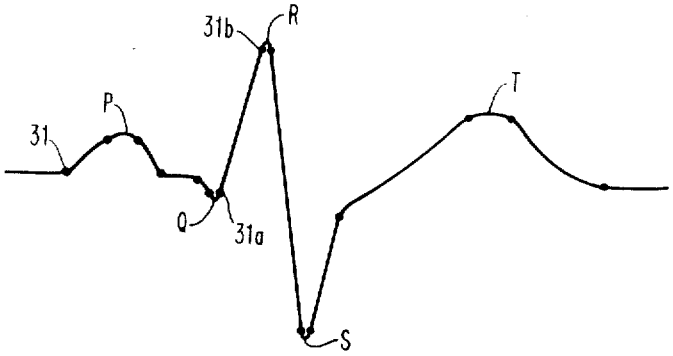
Figure 2B:
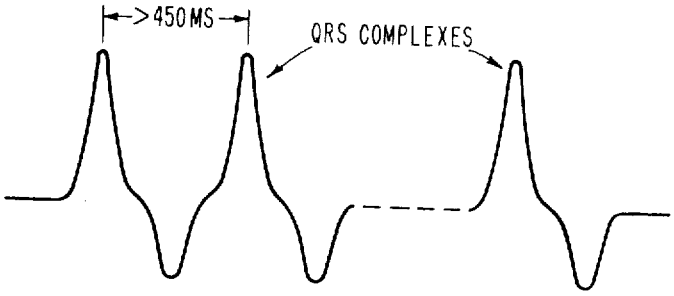
Figure 2C:
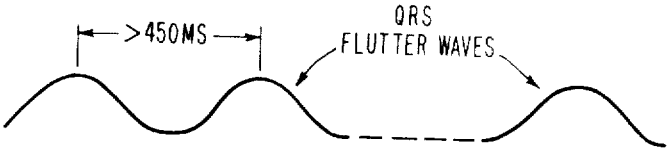
Figure 2D:
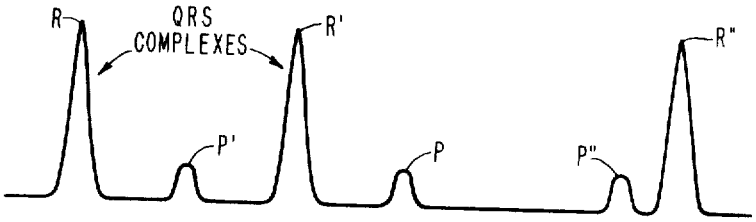
Figure 3:
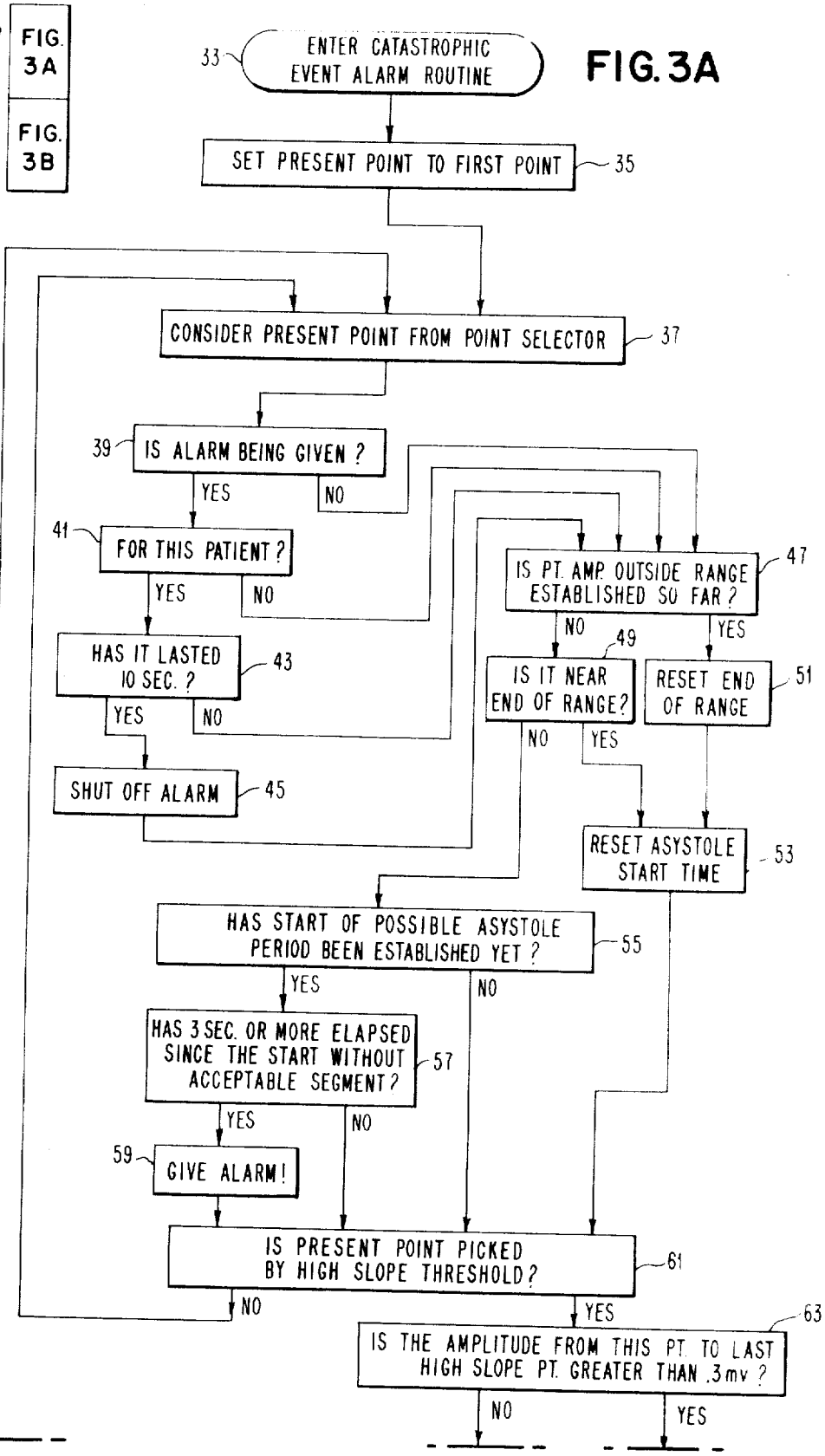
Figure 3B:
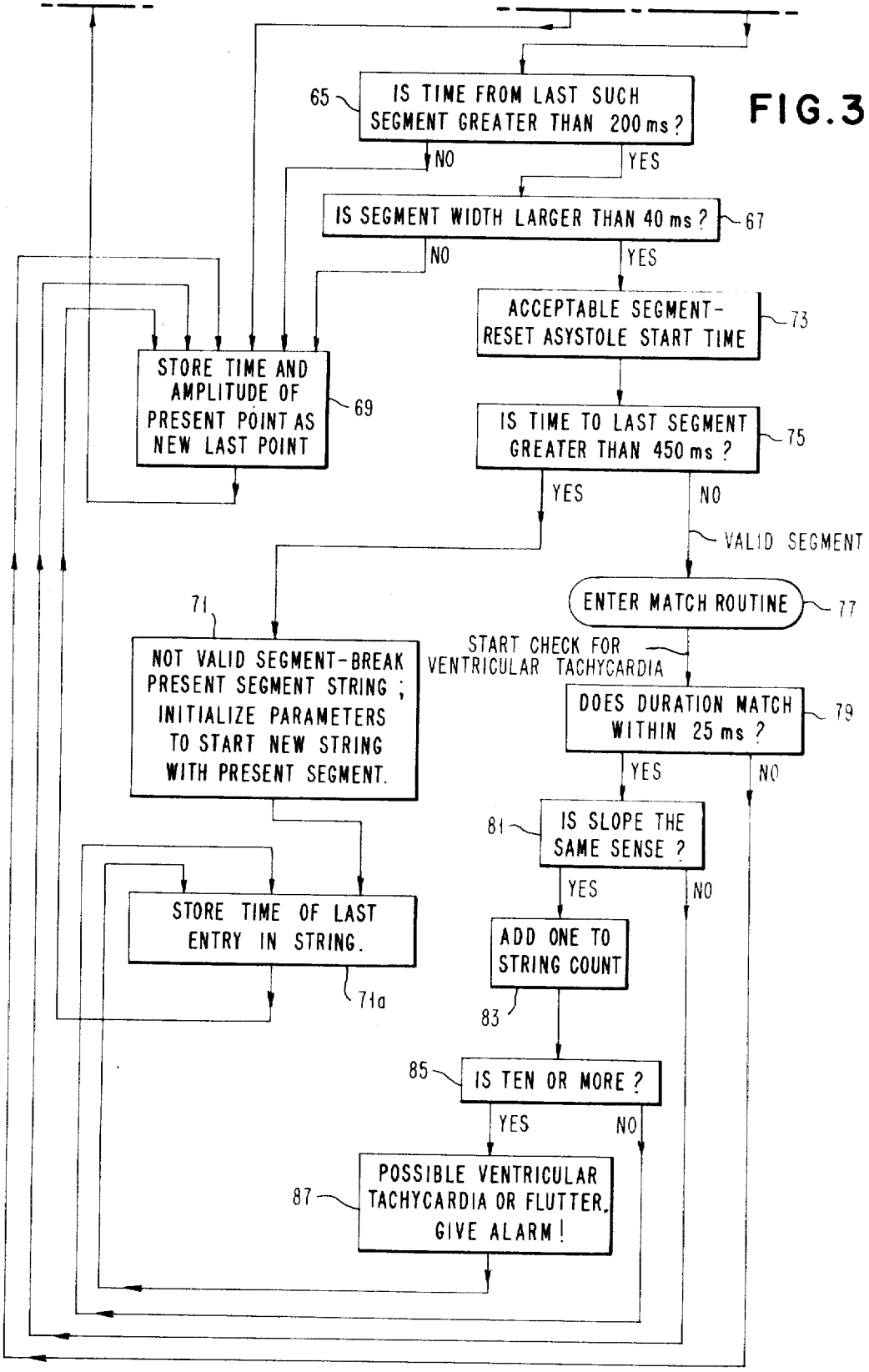
Figure 4:
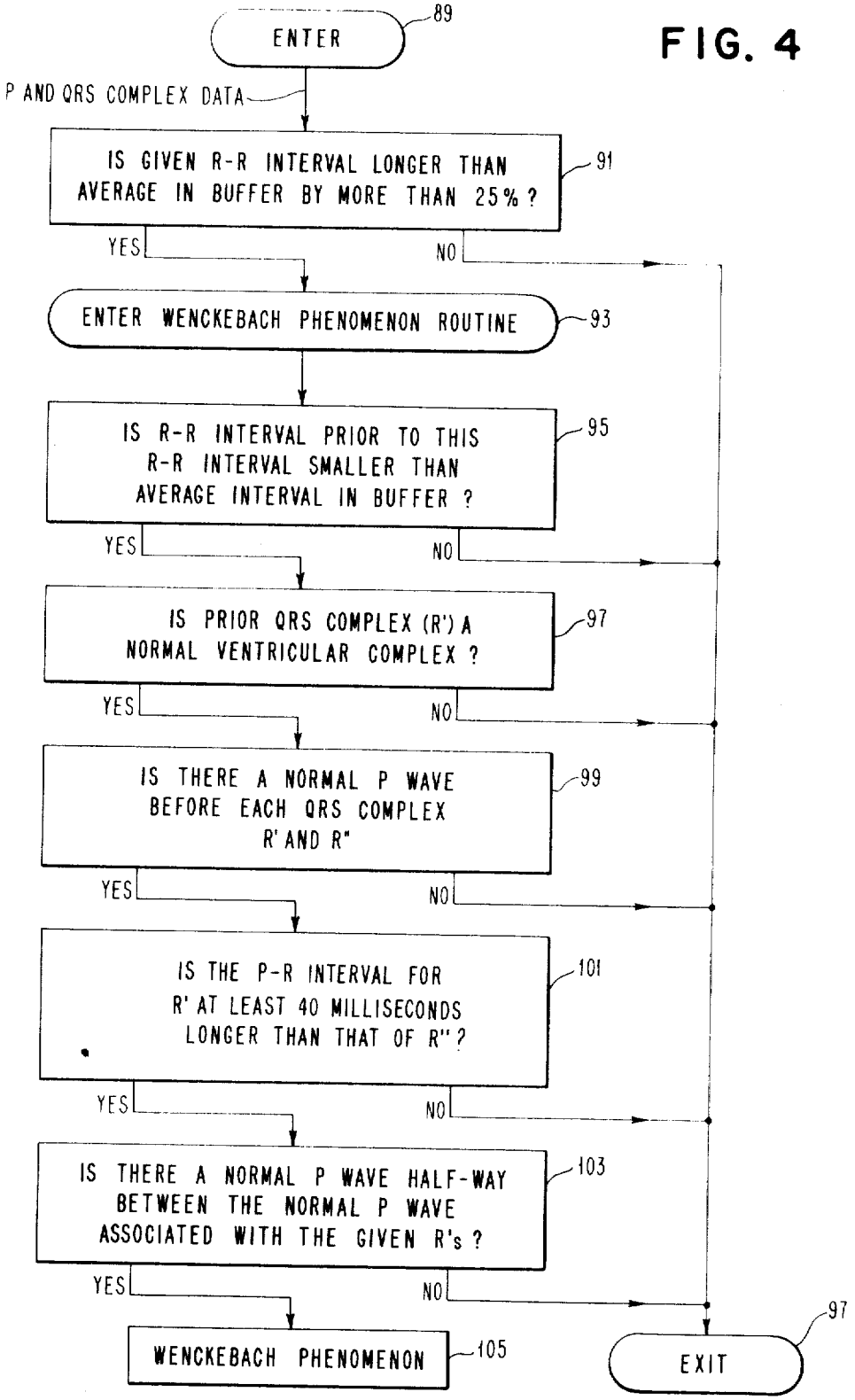

DEFENSIVE PUBLICATION

UNITED STATES PATENT OFFICE

Published at the request of the applicant or owner in accordance with the Notice of Dec. 16, 1969, 869 O.G. 687. The abstracts of Defensive Publication applications are identified by distinctly numbered series and are arranged chronologically. The heading of each abstract indicates the number of pages of specification, including claims and sheets of drawings contained in the application as originally filed. The files of these applications are available to the public for inspection and reproduction may be purchased for 30 cents a sheet.

Defensive Publication applications have not been examined as to the merits of alleged invention. The Patent Office makes no assertion as to the novelty of the disclosed subject matter.

PUBLISHED NOVEMBER 27, 1973

916. O.G. 1212

T916,007

TWO-MODE ECG MONITORING SYSTEM

Raymond E. Bonner, Yorktown Heights, N.J., assignor to International Business Machines Corporation, Armonk, N.Y.

Continuation of abandoned application Ser. No. 135,681, Apr. 20, 1971. This application Apr. 3, 1973, Ser. No. 347,522

Int. Cl. G06f *15/42, 9/18*

U.S. Cl. 340—172.5

5 Sheets Drawing. 32 Pages Specification

The monitoring and analysis of electrocardiographic signals, in the coronary care unit, to identify arrhythmias, and the like, requires the immediate determination of catastrophic event information and the subsequent determination of trend information. To achieve this end, a general purpose digital computer is shown generally within block 1 operated to continuously monitor, real time, selected ECG data and provide an alarm upon the occurrence of a catastrophic event. In addition, the computer is operated as represented by switch 27 and control block 29 to intermittently store, real time, fixed intervals of the selected ECG data. After each fixed interval of selected ECG data is stored in disk store 23, for example, the computer is operated to analyze for ECG events indicative of cardiac trends. During this trend analysis operation no selected ECG data is stored but the computer is still undergoing the catastrophic event analysis operation. After each trend analysis operation, another fixed interval of selected ECG data is stored. During each storage operation, background operations may be performed, in addition to the catastrophic event analysis operation.

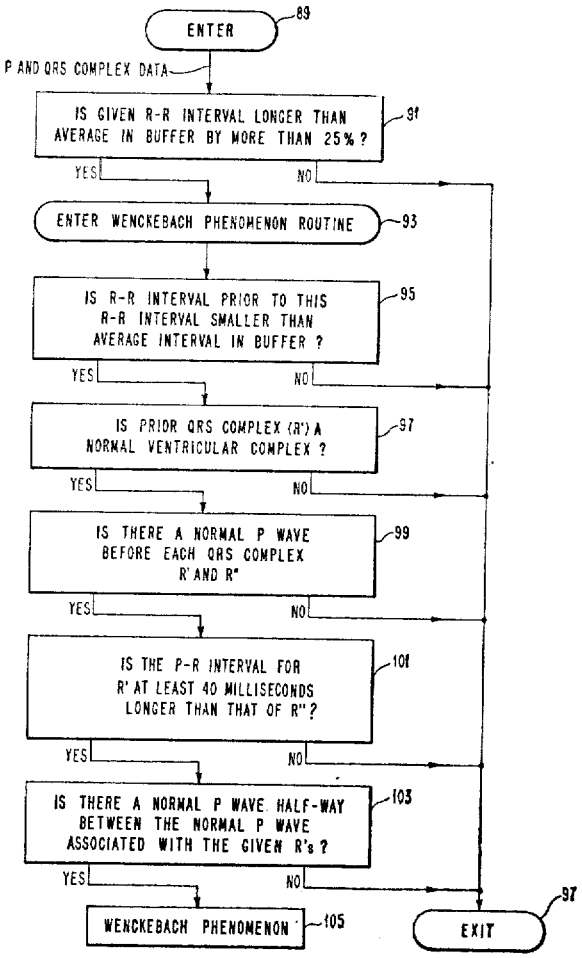

TWO-MODE ECG MONITORING SYSTEM

Original Filed April 20, 1971 5 Sheets-Sheet 1

INVENTOR
RAYMOND E. BONNER
BY John A. Jordan
ATTORNEY

TWO-MODE ECG MONITORING SYSTEM

Original Filed April 20, 1971 5 Sheets-Sheet 3

TWO-MODE ECG MONITORING SYSTEM

Original Filed April 20, 1971 5 Sheets-Sheet 4

TWO-MODE ECG MONITORING SYSTEM

Original Filed April 20, 1971 5 Sheets-Sheet 5